(12) United States Patent
Salciccioli et al.

(10) Patent No.: US 10,787,399 B2
(45) Date of Patent: Sep. 29, 2020

(54) PREPARATION AND USE OF PHENYLSTYRENE

(71) Applicant: ExxonMobil Chemical Patents Inc., Baytown, TX (US)

(72) Inventors: Michael Salciccioli, Houston, TX (US); Alan A. Galuska, Huffman, TX (US); Ranjita Ghose, Houston, TX (US); Doron Levin, Highland Park, NJ (US); Mosha H. Zhao, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 124 days.

(21) Appl. No.: 15/946,077

(22) PCT Filed: Oct. 14, 2016

(86) PCT No.: PCT/US2016/057168
§ 371 (c)(1),
(2) Date: Apr. 5, 2018

(87) PCT Pub. No.: WO2017/087105
PCT Pub. Date: May 26, 2017

(65) Prior Publication Data
US 2018/0258011 A1  Sep. 13, 2018

Related U.S. Application Data

(60) Provisional application No. 62/258,165, filed on Nov. 20, 2015.

(30) Foreign Application Priority Data

Jan. 26, 2016 (EP) .................................. 16152671

(51) Int. Cl.
C07C 2/74 (2006.01)
C07C 2/66 (2006.01)
(Continued)

(52) U.S. Cl.
CPC .................. *C07C 2/74* (2013.01); *C07C 2/66* (2013.01); *C07C 5/333* (2013.01); *C07C 5/367* (2013.01);
(Continued)

(58) Field of Classification Search
CPC .. C07C 2/74; C07C 6/06; C07C 5/367; C07C 5/266; C07C 5/333
See application file for complete search history.

(56) References Cited

U.S. PATENT DOCUMENTS 4,962,253 A 10/1990 Dubois
6,037,513 A 3/2000 Chang et al.
(Continued)

FOREIGN PATENT DOCUMENTS

EP 2 639 246 B 11/2014
JP 04202145 A 3/1995
(Continued)

OTHER PUBLICATIONS

Borodina et al. (Hydroalkylation of benzene and ethylbenzene over metal containing zeolite catalysts, 2009, Microporous and mesoporous materials, vol. 105, pp. 181-188) (Year: 2009).*
(Continued)

*Primary Examiner* — Youngsul Jeong
(74) *Attorney, Agent, or Firm* — Kevin M. Faulkner

(57) ABSTRACT

A process for producing phenylstyrene comprises contacting benzene with hydrogen in the presence of a hydroalkylation catalyst under conditions effective to produce a hydroalkylation product comprising cyclohexylbenzene. At least part of the cyclohexylbenzene is then contacted with ethylbenzene in the presence of a transalkylation catalyst under conditions effective to produce a transalkylation product comprising cyclohexylethylbenzene and/or with ethylene in the presence of an alkylation catalyst under conditions
(Continued)

effective to produce an alkylation product comprising cyclohexylethylbenzene. At least part of the cyclohexylethylbenzene is then contacted with a dehydrogenation catalyst under conditions effective to produce a dehydrogenation product comprising phenylstyrene.

21 Claims, 4 Drawing Sheets

(51) Int. Cl.
  *C07C 5/333*   (2006.01)
  *C07C 5/367*   (2006.01)
  *C07C 6/12*   (2006.01)
  *C07C 6/06*   (2006.01)

(52) U.S. Cl.
  CPC ............... *C07C 6/06* (2013.01); *C07C 6/126* (2013.01); *C07C 2521/02* (2013.01); *C07C 2521/04* (2013.01); *C07C 2521/06* (2013.01); *C07C 2521/08* (2013.01); *C07C 2523/02* (2013.01); *C07C 2523/04* (2013.01); *C07C 2523/06* (2013.01); *C07C 2523/10* (2013.01); *C07C 2523/14* (2013.01); *C07C 2523/18* (2013.01); *C07C 2523/26* (2013.01); *C07C 2523/28* (2013.01); *C07C 2523/30* (2013.01); *C07C 2523/34* (2013.01); *C07C 2523/36* (2013.01); *C07C 2523/40* (2013.01); *C07C 2523/42* (2013.01); *C07C 2523/44* (2013.01); *C07C 2523/46* (2013.01); *C07C 2523/62* (2013.01); *C07C 2523/72* (2013.01); *C07C 2523/745* (2013.01); *C07C 2523/75* (2013.01); *C07C 2523/755* (2013.01); *C07C 2529/08* (2013.01); *C07C 2529/18* (2013.01); *C07C 2529/70* (2013.01); *C07C 2601/14* (2017.05)

(56) References Cited

U.S. PATENT DOCUMENTS

| | | | |
|---|---|---|---|
| 7,485,762 B2 * | 2/2009 | Lee | ............ C07C 1/24 585/469 |
| 7,939,700 B2 | 5/2011 | Clark et al. | |
| 9,328,053 B2 | 5/2016 | Bai et al. | |
| 9,663,417 B2 | 5/2017 | Dakka et al. | |
| 9,896,393 B2 | 2/2018 | Salciccioli et al. | |
| 2008/0241428 A1 | 10/2008 | Harris et al. | |
| 2011/0180784 A1 | 7/2011 | Shukla et al. | |
| 2013/0245199 A1 | 9/2013 | Mruk et al. | |
| 2014/0275606 A1 | 9/2014 | Bai et al. | |

FOREIGN PATENT DOCUMENTS

| | | | | |
|---|---|---|---|---|
| JP | 09-216839 A | | 8/1997 | |
| JP | 09216839 A | * | 8/1997 | ............. C07C 15/50 |
| WO | 2005/035468 A | | 4/2005 | |
| WO | 2010/138248 A | | 12/2010 | |

OTHER PUBLICATIONS

Rivera et al. (A general approach to fabricate Fe3O4 nanoparticles decorated with Pd, Au, and Rh: Magnetically recoverable and reusable catalysts for Suzuki C—C cross-coupling reactions, hydrogenation, and sequential reactions, 2013, Chemistry—A European Journal, vol. 19, pp. 11963-11974) (Year: 2013).*

Qiu et al. (Synthesis of cyclohexylbenzene by hydroalkylation of benzene over Pd/H binary catalyst, 2007, Chinese Journal of Catalysis, vol. 28, Issue 3, pp. 246-250) (Year: 2007).*

Borodina, I.B., et al., "Hydroalkylation of benzene and ethylbenzene over metal-containing zeolite catalysts" Petroleum Chemistry, vol. 49, No. 1, pp. 66-73, 2009.

Gustafsson, A., et al., "Electrical degradation of homo- and copolymers of styrenes and of styrene/2-vinylnaphthalene", Polymer Engineering and Science, vol. 33,No. 9, p. 549-558, 1993.

Anuradha, R. et al. "Pore Size Independent Rejioselective Cuclohexylation of Ethylbenzene", Journal of Molecular Catalysis A: Chemical vol. 272, pp. 198-206, 2007.

Sugi, Y., et al. "The Ethylation of Biphenyl over H-Mordenite: Reactivities of the Intermediates in the Catalysis" Journal of Molecular Catalysis A: Chemical, vol. 285, pp. 101-110, 2008.

Rivera, F., et al., "A Genera Approach to Fabricate Fe3O4 Nanoparticles Decorated with Pd, Au, and Rh: Magnetically Recoverable and Reusable Catalysts for Suzuki C—C Cross-Coupling Reactions, Hydrogenation, and Sequential Reactions", Chemistry—A European Journal, vol. 19, pp. 11963-11974, 2013.

* cited by examiner

PREPARATION AND USE OF PHENYLSTYRENE

CROSS-REFERENCE OF RELATED APPLICATIONS

This application is a National Phase Application claiming priority to PCT/US2016/057168, filed Oct. 14, 2016, which claims priority to and the benefit of U.S. Ser. No. 62/258,165, filed Nov. 20, 2015, and EP application 16152671.0, filed Jan. 26, 2016.

FIELD OF THE INVENTION

This invention relates to a process for preparing phenylstyrene, in particular, the para-isomer of phenylstyrene, 4-vinylbiphenyl, and its use in the production of polymers.

BACKGROUND OF THE INVENTION

Styrene is an important precursor to polystyrene and related polymers. It is produced industrially by the dehydrogenation of ethylbenzene. Approximately 25 million tonnes (55 billion pounds) of styrene were produced in 2010.

Phenylstyrene, when polymerized alone or with other monomers, has been shown to produce polymers with attractive properties for a variety of potential applications. For example, phenylstyrene has been proposed as a partial replacement for styrene in the production of polymers having improved thermal stability (Borodina et al., *Petroleum Chemistry*, 49 (2009), 66) or improved electrical stability (Gustafsson et al., *Polymer Engineering and Science*, 33 (1993) 549).

Of the various isomers of phenylstyrene, the para-isomer, 4-vinylbiphenyl, has been proposed for use in a number of electronic devices. In one example, poly(4-vinylbiphenyl) is proposed as an improved polymer additive for semiconductor devices (US 2011/0180784), whereas in another example 4-vinylbiphenyl is identified as a monomer (either alone or with a styrene comonomer) for films for use in optical devices, such as liquid crystal displays (US 2008/0241428).

However, no economically viable process for the production of phenylstyrene currently exists and hence there is significant interest in developing a synthesis route for phenylstyrene that would enable its promising properties to be realized at a commercially acceptable scale and cost.

SUMMARY OF THE INVENTION

According to the present invention, a heterogeneously catalyzed series of reactions has been identified to produce phenylstyrene from benzene and ethylbenzene (or benzene and ethylene) as feedstocks. The reaction sequence involves hydroalkylation of benzene to produce cyclohexylbenzene, followed by conversion of cyclohexylbenzene to cyclohexylethylbenzene either by transalkylation with ethylbenzene or alkylation with ethylene, then dehydrogenation of the cyclohexylethylbenzene to produce phenylstyrene. Alternatively, cyclohexylethylbenzene can be supplied as a feedstock. In such aspects, the reaction sequence involves conversion of cyclohexylethylbenzene either by transalkylation with ethylbenzene or alkylation with ethylene, then dehydrogenation of the cyclohexylethylbenzene to produce phenylstyrene. The dehydrogenation process can be conducted in two separate reaction steps or in a single combined step. A variation of this process involves dehydrogenation of the cyclohexylbenzene to biphenyl followed by ethylation to produce ethylbiphenyl, and then dehydrogenation to produce the desired phenylstyrene. Yet alternatively, biphenyl can be supplied as a feedstock. In such aspects, the reaction sequence involves ethylation of the biphenyl to produce ethylbiphenyl, and then dehydrogenation to produce the desired phenylstyrene.

Thus, in one aspect, the invention resides in a process for producing phenylstyrene, the process comprising:
(a1) contacting benzene with hydrogen in the presence of a hydroalkylation catalyst under conditions effective to produce a hydroalkylation product comprising cyclohexylbenzene;
(b1) converting at least part of the cyclohexylbenzene from (a1) to cyclohexylethylbenzene by contacting the cyclohexylbenzene with ethylbenzene in the presence of a transalkylation catalyst under conditions effective to produce a transalkylation product comprising cyclohexylethylbenzene; and/or contacting the cyclohexylbenzene with ethylene in the presence of an alkylation catalyst under conditions effective to produce an alkylation product comprising cyclohexylethylbenzene; and
(c1) contacting at least part of the cyclohexylethylbenzene from (b1) with at least one dehydrogenation catalyst under conditions effective to produce a dehydrogenation product comprising phenylstyrene.

In another aspect, the invention resides in a process for producing phenylstyrene, the process comprising:
(a2) converting cyclohexylbenzene to cyclohexylethylbenzene by contacting the cyclohexylbenzene with ethylbenzene in the presence of a transalkylation catalyst under conditions effective to produce a transalkylation product comprising cyclohexylethylbenzene; and/or contacting the cyclohexylbenzene with ethylene in the presence of an alkylation catalyst under conditions effective to produce an alkylation product comprising cyclohexylethylbenzene; and
(b2) contacting at least part of the cyclohexylethylbenzene from (a2) with at least one dehydrogenation catalyst under conditions effective to produce a dehydrogenation product comprising phenylstyrene.

In one embodiment, the contacting (c1) or (b2) to convert the cyclohexylethylbenzene to phenylstyrene is conducted in a single step.

In another embodiment, the contacting (c1) or (b2) comprises:
i) contacting at least part of the cyclohexylethylbenzene from (b1) with a first dehydrogenation catalyst to produce a first dehydrogenation product comprising ethylbiphenyl; and
(ii) contacting at least part of the ethylbiphenyl from (i) with a second dehydrogenation catalyst to produce a second dehydrogenation product comprising phenylstyrene.

In another aspect, the invention resides in a process for producing phenylstyrene, the process comprising:
(a3) contacting benzene with hydrogen in the presence of a hydroalkylation catalyst under conditions effective to produce a hydroalkylation product comprising cyclohexylbenzene;
(b3) contacting at least part of the cyclohexylbenzene from (a2) with a first dehydrogenation catalyst to produce a first dehydrogenation product comprising biphenyl;
(c3) contacting at least part of the biphenyl from (b2) with an alkylation catalyst and ethylene under conditions effective to produce an alkylation product comprising ethylbiphenyl; and (d3) contacting at least part of the ethylbiphenyl from (c2) with a second dehydrogenation catalyst to produce a second dehydrogenation product comprising phenylstyrene.

In another aspect, the invention resides in a process for producing phenylstyrene, the process comprising:

(a4) contacting biphenyl with an alkylation catalyst and ethylene under conditions effective to produce an alkylation product comprising ethylbiphenyl; and (b4) contacting at least part of the ethylbiphenyl from (a4) with a second dehydrogenation catalyst to produce a second dehydrogenation product comprising phenylstyrene.

DETAILED DESCRIPTION OF THE EMBODIMENTS

Figure 1:
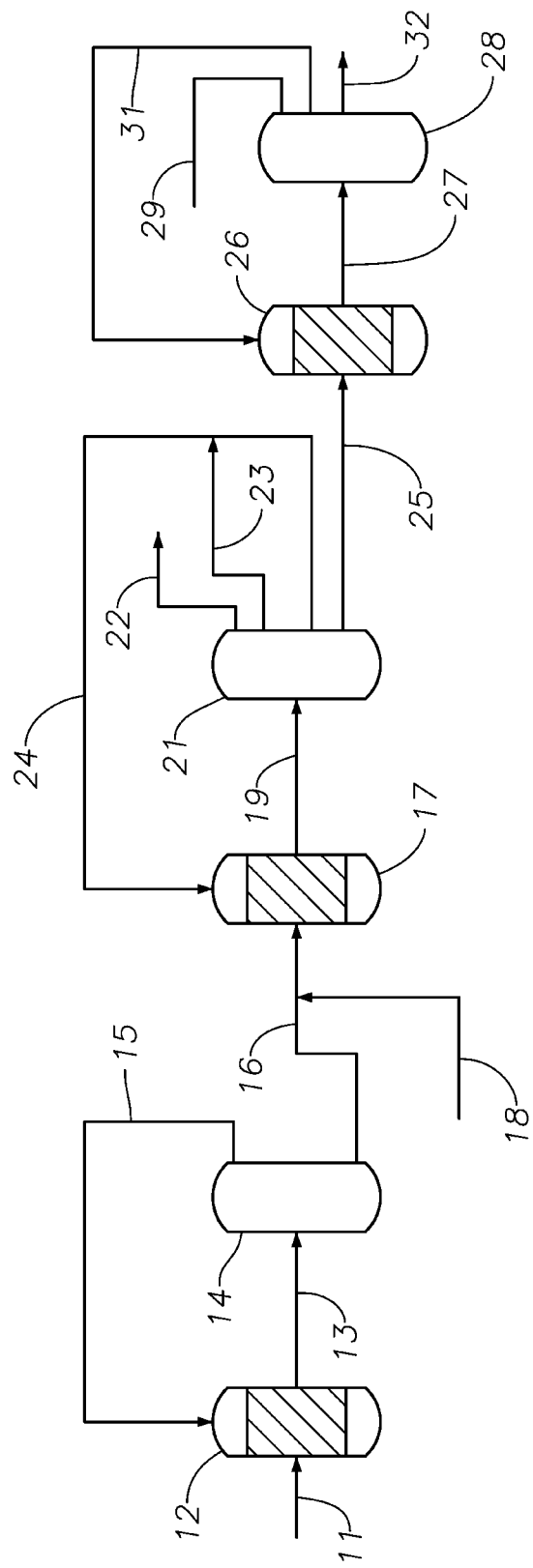
FIG. 1 is a simplified process flow diagram showing the major reaction and separation steps for a process for producing phenylstyrene from benzene and ethylbenzene according to one example of the present invention.

The present invention provides a sequence of heterogeneously catalyzed reactions for the production of phenylstyrene from the readily available feedstocks (i) benzene and (ii) ethylbenzene or ethylene and benzene reacting in situ. The overall sequence route is net positive in hydrogen production and hence, in addition to producing phenylstyrene, could provide a valuable source of hydrogen for a refinery and/or chemical plant. Preferably, the sequence of heterogeneously catalyzed reactions enables the production of phenylstyrene in quantities of greater than about 5 kg/hr, preferably greater than about 500 kg/hr, preferably greater than about 5000 kg/hr, and preferably greater than about 35000 kg/hr.

In some embodiments, the novel reaction sequence involves initially contacting benzene with hydrogen in the presence of a hydroalkylation catalyst under conditions so as hydroalkylate the benzene to cyclohexylbenzene. The next reaction stage involves transalkylation of the resultant cyclohexylbenzene with ethylbenzene to produce cyclohexylethylbenzene. The ethylbenzene may be produced prior to the transalkylation reaction and fed as ethylbenzene to the relevant reaction zone. Alternately or additionally, benzene and ethylene may be fed to the transalkylation reaction zone such that at least part of the ethylbenzene is formed in situ. Finally, as an alternative or supplement to transalkylation, ethylene may be fed in a second reaction zone, possibly under different conditions or over a different catalyst, to alkylate the cyclohexylbenzene directly to cyclohexylethylbenzene. The final reaction stage includes the dehydrogenation of cyclohexylethylbenzene to produce the phenylstyrene product and can be effected in a single step or in two separate steps. In the latter case, the cyclohexylethylbenzene is dehydrogenated to ethylbiphenyl in a first step and then the ethylbiphenyl is dehydrogenated to the desired phenylstyrene product in a second step.

The overall reaction sequence, in which the cyclohexylbenzene is transalkylated with ethylbenzene to produce cyclohexylethylbenzene, may summarized by the following reaction scheme, in which the floating bond associated with the ethyl group denotes that the position of the ethyl group can vary.

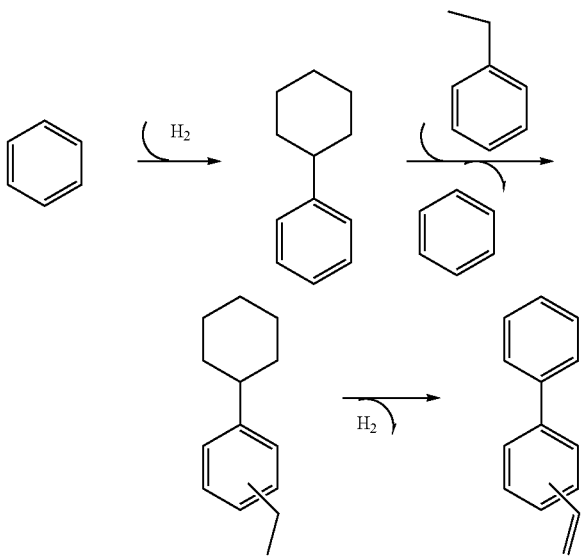

Overall, the selectivity toward cyclohexylethylbenzene is 50% or more, preferably 60% or more, preferably 70% or more, preferably 80% or more (moles cyclohexylethylbenzene produced per mole cyclohexylbenzene consumed).

The overall reaction sequence, in which cyclohexylbenzene is alkylated with ethylene to produce cyclohexylethylbenzene, may be summarized by the following reaction scheme, again in which the floating bond associated with the ethyl group denotes that the position of the ethyl group can vary.

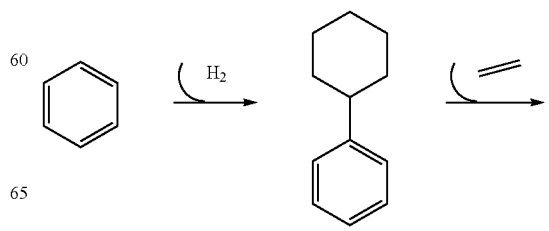

-continued

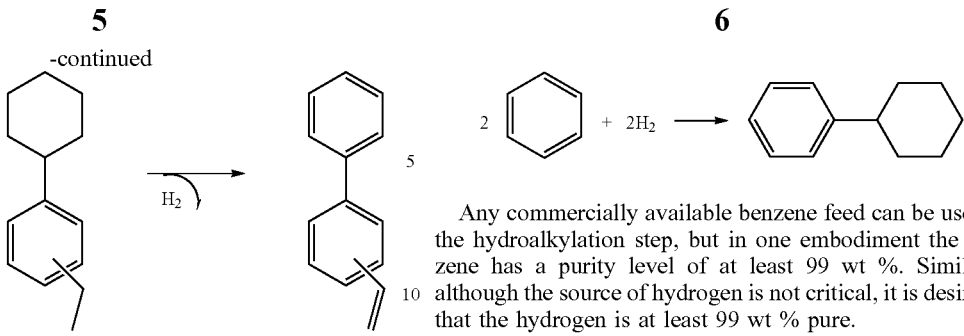

In other embodiments, the novel reaction sequence again includes hydroalkylation of benzene to produce cyclohexylbenzene, but the next reactive step includes dehydrogenating at least part of the cyclohexylbenzene to produce a first dehydrogenation product comprising biphenyl. At least part of the biphenyl is then alkylated with ethylene to produce an alkylation product comprising ethylbiphenyl. In the final reactive step, at least part of the resultant ethylbiphenyl from (c2) is dehydrogenated to produce a second dehydrogenation product comprising phenylstyrene. In this case, the overall reaction sequence may be summarized by the following reaction scheme, again in which the floating bond associated with the ethyl group denotes that the position of the ethyl group can vary.

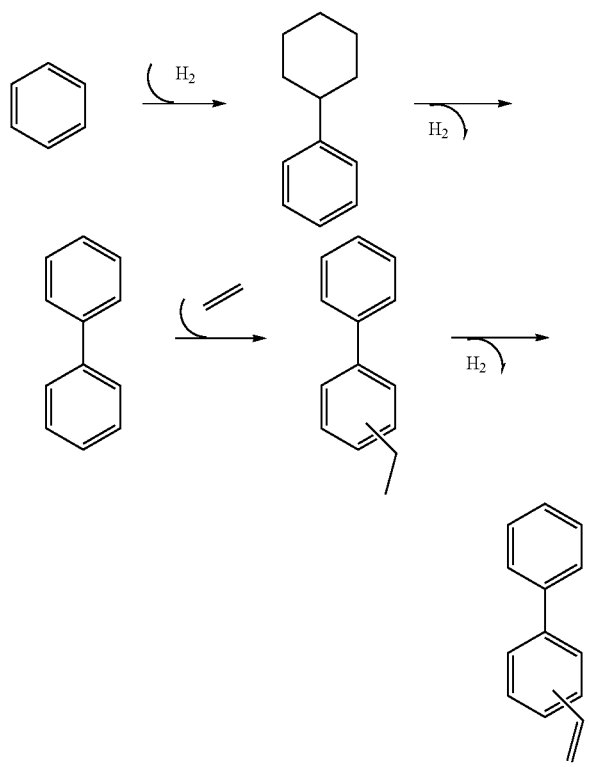

Hydroalkylation of Benzene to Cyclohexylbenzene

The first step in the present reaction sequence for producing phenylstyrene comprises contacting benzene with hydrogen in the presence of a hydroalkylation catalyst. The catalyst and conditions are selected such that the benzene is selectively hydrogenated to cyclohexene, which then alkylates additional benzene to produce cyclohexylbenzene. The overall hydroalkylation reaction may be summarized as follows:

Any commercially available benzene feed can be used in the hydroalkylation step, but in one embodiment the benzene has a purity level of at least 99 wt %. Similarly, although the source of hydrogen is not critical, it is desirable that the hydrogen is at least 99 wt % pure.

In certain embodiments, the total feed to the hydroalkylation step contains less than 1000 ppm, such as less than 500 ppm, for example, less than 100 ppm water. In addition, the total feed may contain less than 100 ppm, such as less than 30 ppm, for example, less than 3 ppm sulfur and less than 10 ppm, such as less than 1 ppm, for example, less than 0.1 ppm nitrogen.

Hydrogen can be supplied to the hydroalkylation step over a wide range of values, but the hydrogen supply is desirably arranged such that the molar ratio of hydrogen to benzene in the hydroalkylation feed is from about 0.15:1 to about 15:1, such as from about 0.4:1 to about 4:1, for example, from about 0.4 to about 0.9:1.

In addition to the benzene and hydrogen, a diluent, which is substantially inert under hydroalkylation conditions, may be supplied to the hydroalkylation reaction. In certain embodiments, the diluent is a hydrocarbon, in which the desired cycloalkylaromatic product, in this case cyclohexylbenzene, is soluble, such as a straight chain paraffinic hydrocarbon, a branched chain paraffinic hydrocarbon, and/or a cyclic paraffinic hydrocarbon. Examples of suitable diluents are decane and cyclohexane. Cyclohexane is a particularly attractive diluent since it is a by-product of the hydroalkylation reaction.

Although the amount of diluent is not narrowly defined, advantageously the diluent is added in an amount such that the weight ratio of the diluent to the aromatic compound is at least 1:100; for example, at least 1:10, but no more than 10:1, for example, no more than 4:1.

The hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones, in which at least the hydrogen is introduced to the reaction in stages. Suitable reaction temperatures are from about 100° C. to about 400° C., such as from about 125° C. to about 250° C., while suitable reaction pressures are from about 100 kPa to about 7,000 kPa, such as from about 500 kPa to about 5,000 kPa.

The catalyst employed in the hydroalkylation reaction is typically a bifunctional catalyst comprising a hydrogenation component and a solid acid alkylation component, typically a molecular sieve. The catalyst may also include a binder such as clay, alumina, silica and/or metal oxides. The latter may be either naturally occurring or in the form of gelatinous precipitates or gels, including mixtures of silica and metal oxides. Naturally occurring clays, which can be used as a binder, include those of the montmorillonite and kaolin families, which families include the subbentonites and the kaolins commonly known as Dixie, McNamee, Georgia, and Florida clays or others in which the main mineral constituent is halloysite, kaolinite, dickite, nacrite, or anauxite. Such clays can be used in the raw state as originally mined or initially subjected to calcination, acid treatment, or chemical modification. Suitable metal oxide binders include silica, alumina, zirconia, titania, silica-alumina, silica-magnesia, silica-zirconia, silica-thoria, silica-beryllia, silica-titania, as well as ternary compositions such as silica-alumina-thoria, silica-alumina-zirconia, silica-alumina-magnesia and silica-magnesia-zirconia.

Any known hydrogenation metal or compound thereof can be employed as the hydrogenation component of the hydroalkylation catalyst, although suitable metals include palladium, ruthenium, nickel, zinc, tin, cobalt, silver, gold, platinum, and compounds and mixtures thereof, with palladium being particularly advantageous. In certain embodiments, the amount of hydrogenation metal present in the catalyst is between about 0.05 and about 10 wt %, such as between about 0.1 and about 5 wt %, of the catalyst.

In one embodiment, the solid acid alkylation component comprises a large pore molecular sieve having a Constraint Index (as defined in U.S. Pat. No. 4,016,218) less than 2. Suitable large pore molecular sieves include zeolite beta, zeolite Y, Ultrastable Y (USY), Dealuminized Y (Deal Y), mordenite, ZSM-3, ZSM-4, ZSM-18, and ZSM-20. Zeolite ZSM-4 is described in U.S. Pat. No. 4,021,447. Zeolite ZSM-20 is described in U.S. Pat. No. 3,972,983. Zeolite Beta is described in U.S. Pat. No. 3,308,069, and Re. No. 28,341. Low sodium Ultrastable Y molecular sieve (USY) is described in U.S. Pat. No. 3,293,192 and U.S. Pat. No. 3,449,070. Dealuminized Y zeolite (Deal Y) may be prepared by the method found in U.S. Pat. No. 3,442,795. Zeolite UHP-Y is described in U.S. Pat. No. 4,401,556. Mordenite is a naturally occurring material, but is also available in synthetic forms, such as TEA-mordenite (i.e., synthetic mordenite prepared from a reaction mixture comprising a tetraethylammonium directing agent). TEA-mordenite is disclosed in U.S. Pat. No. 3,766,093 and U.S. Pat. No. 3,894,104. Preferred large pore molecular sieves for use as the solid acid alkylation component of the hydroalkylation catalyst comprise molecular sieves of the BEA and FAU structure type.

In another, more preferred embodiment, the solid acid alkylation component comprises a molecular sieve of the MCM-22 family. The term "MCM-22 family material" (or "material of the MCM-22 family" or "molecular sieve of the MCM-22 family"), as used herein, includes one or more of:
  molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated herein by reference);
  molecular sieves made from a common second degree building block, being a 2-dimensional tiling of such MWW framework topology unit cells, forming a monolayer of one unit cell thickness, preferably one c-unit cell thickness;
  molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and
  molecular sieves made by any regular or random 2-dimensional or 3-dimensional combination of unit cells having the MWW framework topology.

Molecular sieves of the MCM-22 family generally have an X-ray diffraction pattern including d-spacing maxima at 12.4±0.25, 6.9±0.15, 3.57±0.07, and 3.42±0.07 Angstrom. The X-ray diffraction data used to characterize the material are obtained by standard techniques using the K-alpha doublet of copper as the incident radiation and a diffractometer equipped with a scintillation counter and associated computer as the collection system. Molecular sieves of the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in EP 0 293 032), ITQ-1 (described in U.S. Pat. No. 6,077,498), and ITQ-2 (described in WO 97/17290), MCM-36 (described in U.S. Pat. No. 5,250,277), MCM-49 (described in U.S. Pat. No. 5,236,575), MCM-56 (described in U.S. Pat. No. 5,362,697), and mixtures of two or more thereof. Related zeolites to be included in the MCM-22 family are UZM-8 (described in U.S. Pat. No. 6,756,030) and UZM-8HS (described in U.S. Pat. No. 7,713,513), both of which are also suitable for use as the molecular sieve of the MCM-22 family.

Although the hydroalkylation reaction, especially using an MCM-22 family zeolite catalyst, is highly selective towards cyclohexylbenzene, the effluent from the hydroalkylation reaction will inevitably contain some dicyclohexylbenzene by-product. Depending on the amount of this dicyclohexylbenzene, it may be desirable to either (a) transalkylate the dicyclohexylbenzene with additional benzene or (b) dealkylate the dicyclohexylbenzene to maximize the production of the desired monoalkylated species.

Transalkylation with additional benzene may be conducted in a transalkylation reactor, separate from the hydroalkylation reactor, over a suitable transalkylation catalyst, such as a molecular sieve of the MCM-22 family, zeolite beta, MCM-68 (see U.S. Pat. No. 6,014,018), zeolite Y, and/or mordenite. The transalkylation reaction is desirably conducted under at least partial liquid phase conditions, which suitably include a temperature of about 100 to about 300° C., a pressure of about 800 to about 3500 kPa, a weight hourly space velocity of about 1 to about 10 $hr^{-1}$ on total feed, and a benzene/dicyclohexylbenzene weight ratio of about 1:1 to about 5:1.

Dealkylation or cracking may also be affected in a reactor separate from the hydroalkylation reactor, such as a reactive distillation unit, at a temperature of about 150° C. to about 500° C. and a pressure of 15 to 500 psig (200 to 3550 kPa) over an acid catalyst such as an aluminosilicate, an aluminophosphate, a silicoaluminphosphate, amorphous silica-alumina, an acidic clay, a mixed metal oxide, such as $WO_x/ZrO_2$, phosphoric acid, sulfated zirconia, and mixtures thereof. Desirably, the acid catalyst includes at least one aluminosilicate, aluminophosphate, or silicoaluminphosphate of the FAU, AEL, AFI, and MWW family. Unlike transalkylation, dealkylation can be conducted in the absence of added benzene, although it may be desirable to add benzene to the dealkylation reaction to reduce coke formation. In this case, the weight ratio of benzene to poly-alkylated aromatic compounds in the feed to the dealkylation reaction is desirably from 0 to about 0.9, such as from about 0.01 to about 0.5. Similarly, although the dealkylation reaction can be conducted in the absence of added hydrogen, hydrogen is advantageously introduced into the dealkylation reactor to assist in coke reduction. Suitable hydrogen addition rates are such that the molar ratio of hydrogen to poly-alkylated aromatic compound in the total feed to the dealkylation reactor is from about 0.01 to about 10.

Another significant by-product of the hydroalkylation reaction is cyclohexane. Although a $C_6$-rich stream comprising cyclohexane and unreacted benzene can be readily removed from the hydroalkylation reaction effluent by distillation, owing to the similarity in the boiling points of benzene and cyclohexane, the $C_6$-rich stream is difficult to further separate by simple distillation. However, some or all of the $C_6$-rich stream can be recycled to the hydroalkylation reactor to provide not only part of the benzene feed, but also part of the diluents mentioned above.

In some cases, it may be desirable to supply some of the $C_6$-rich stream to a dehydrogenation reaction zone, where the $C_6$-rich stream is contacted with a dehydrogenation catalyst under dehydrogenation conditions sufficient to convert at least part of the cyclohexane in the $C_6$-rich stream portion to benzene, which again can be recycled to the hydroalkylation reaction. The dehydrogenation catalyst may comprise (a) a support, (b) a hydrogenation-dehydrogenation component, and (c) an inorganic promoter. In certain embodiments, the support (a) is selected from the group consisting of silica, a silicate, an aluminosilicate, zirconia, and carbon nanotubes, and preferably comprises silica. Suitable hydrogenation-dehydrogenation components (b) comprise at least one metal selected from Groups 6 to 10 of the Periodic Table of Elements, such as platinum, palladium, and compounds and mixtures thereof. Desirably, the hydrogenation-dehydrogenation component is present in an amount from about 0.1 to about 10 wt % of the catalyst. A suitable inorganic promoter (c) comprises at least one metal or compound thereof selected from Group 1 of the Periodic Table of Elements, such as a potassium compound. The promoter may be present in an amount from about 0.1 to about 5 wt % of the catalyst. Suitable dehydrogenation conditions include a temperature of about 250° C. to about 500° C., a pressure of about atmospheric to about 500 psig (100 to 3550 kPa), a weight hourly space velocity of about 0.2 to about 50 hr$^{-1}$, and a hydrogen to hydrocarbon feed molar ratio of about 0 to about 20.

The cyclohexylbenzene product from the hydroalkylation reaction and any downstream reaction to remove the impurities discussed herein is separated from the reaction effluent (s) by conventional means and is fed to the next stage in the reaction sequence.

Conversion of Cyclohexylbenzene to Phenylstyrene Via Cyclohexylethylbenzene

In certain embodiments, the present reaction sequence for producing phenylstyrene proceeds via conversion of the cyclohexylbenzene generated in the benzene hydroalkylation stage to cyclohexylethylbenzene, followed by dehydrogenation of the cyclohexylethylbenzene.

In one such embodiment, the second reaction stage in the present process comprises transalkylation of the cyclohexylbenzene generated in the hydroalkylation step with ethylbenzene to produce a mixture of cyclohexylethylbenzene isomers in which the ethyl group is located at the 2-, 3-, and 4-positions on the benzene ring (2-, 3-, and 4-isomers). The ethylbenzene required for transalkylation reaction can be provided as a separate feedstock to the transalkylation reaction. Alternately or additionally, benzene and ethylene may be fed to the transalkylation reaction zone such that at least part of the ethylbenzene is formed in situ. Under this embodiment, cyclohexylbenzene can also be directly alkylated by ethylene to form the desired cyclohexylethylbenzene product.

The transalkylation reaction can be conducted over a wide range of conditions but in most embodiments is effected at a temperature from about 50° C. to about 400° C., or about 100° C. to about 400° C., such as about 75° C. to about 250° C., such as from about 100° C. to about 200° C., such as from about 125° C. to 185° C., for example, 125° C. to 175° C. and a pressure from about 100 to about 10,000 kPa-absolute, such as from about 100 to about 3550 kPa-absolute, such as from about 1000 to about 1500 kPa-absolute. The reaction may be conducted in the presence of a solid acid transalkylation catalyst, such as a molecular sieve and, in particular, a molecular sieve having a large pore molecular sieve having a Constraint Index (as defined in U.S. Pat. No. 4,016,218) less than 2 Suitable large pore molecular sieves include zeolite beta, zeolite Y, Ultrastable Y (USY), Dealuminized Y (Deal Y), mordenite, ZSM-3, ZSM-4, ZSM-18, ZSM-20, and mixtures thereof. Other suitable molecular sieves include molecular sieves of the MCM-22 family, including MCM-22 (described in U.S. Pat. No. 4,954,325), PSH-3 (described in U.S. Pat. No. 4,439,409), SSZ-25 (described in U.S. Pat. No. 4,826,667), ERB-1 (described in EP 0 293 032), ITQ-1 (described in U.S. Pat. No. 6,077,498), ITQ-2 (described in WO 97/17290), MCM-36 (described in U.S. Pat. No. 5,250,277), MCM-49 (described in U.S. Pat. No. 5,236,575), MCM-56 (described in U.S. Pat. No. 5,362,697), and mixtures thereof. Related zeolites such as UZM-8 (described in U.S. Pat. No. 6,756,030), and UZM-8HS (described in U.S. Pat. No. 7,713,513) may also be used as the or part of the transalkylation catalyst.

Preferred molecular sieves for the transalkylation catalyst comprise those selected from the group consisting of BEA, FAU, MOR, MFI, MWW framework type molecular sieves, and mixtures thereof.

In some embodiments, the hydroalkylation reaction and the transalkyation reaction can be conducted in the same reaction zone in the presence of a single catalyst having both alkylation and hydrogenation activity or over a combination of a hydroalkylation catalyst and a transalkylation catalyst arranged either as a single mixed bed or as multiple beds in stacked formation. In these embodiments, hydroalkylation between ethylbenzene and benzene can occur to directly produce cyclohexylethylbenzene, or ethylcyclohexylbenzene.

As mentioned above, the product of the transalkylation reaction will comprise a mixture of all the isomers of cyclohexylethylbenzene. However, some applications require specific phenylstyrene isomers (often 4-vinylbiphenyl is desired). For this purpose, the present process can be readily adapted to produce this specific isomer of phenylstyrene by isolating, for example, 1-cyclohexyl-4-ethylbenzene, via separation by boiling or melting point (distillation and/or crystallization) and then recycling the undesired isomer(s) to the transalkylation reactor where substitution of the aromatic ring can occur with ethylbenzene to produce the desired cyclohexylethylbenzene isomer from the undesired cyclohexylethylbenzene isomer. This process is general for producing any isomer or combination of isomers of phenylstyrene, given the ability to separate the corresponding cyclohexylethylbenzene (CHEB) isomers. In this scheme, the transalkylation reaction is used for both net alkylation of cyclohexylbenzene and net isomerization of undesired cyclohexylethylbenzenes.

Preferably, the transalkyation reaction is particularly useful in the formation of the 4-isomer of CHEB and, ultimately, 4-vinylbiphenyl. For example, the transalklation reaction product typically comprises a mixture of CHEB isomers having a ratio of 3- to 4-isomers of about 2:1 and having little to no amount of 2-isomer (e.g., <2 wt %). Preferably, the transalkylation product comprises a mixture of CHEB isomers comprising less than about 2 wt %, or less than about 1 wt %, of the 2-isomer, greater than about 20 wt %, or greater than about 30 wt %, of the 4-isomer, and greater than about 40 wt %, or greater than 50 wt %, of the 3-isomer. Additionally or alternatively, the transalkylation product may comprise a mixture of CHEB isomers comprising less than about 40 wt %, or less than about 30 wt %, of the 4-isomer, and less than about 70 wt %, or less than about 60 wt %, of the 3-isomer.

In addition to cyclohexylethylbenzene, the transalkylation reaction effluent also contains co-produced benzene, as well as residual cyclohexylbenzene and ethylbenzene. The co-produced benzene can be recovered from the effluent and recycled to the hydroalkylation stage, whereas the residual cyclohexylbenzene and ethylbenzene can be removed for recycle back to the transalkylation step.

Transalkylation can also be used to change the isomer distribution of the cyclohexylethylbenzene. Under the scenario where there is one or more desired product isomers, the undesired cyclohexylethylbenzene isomer(s) can be separated and recycled to the transalkylation reactor, whereupon transalkylation with ethylbenzene can result in a different isomer product.

As an alternative or supplement to transalkylation, to add the ethyl group to the core molecule (cyclohexylbenzene), ethyl alkylation via contacting the cyclohexylbenzene feed with ethylene under conditions suitable for alkylation is an option. The cyclohexylbenzene is reacted with ethylene over a solid acid or zeolite catalyst to produce cyclohexylethylbenzene. Conditions suitable for this reaction include temperatures of 100-500° C., preferably between 175-325° C. at pressures between 100-10000 kPa-absolute, preferably between 2000-5000 kPa-absolute. Typically, the feed consists of a monomer (e.g., cyclohexylbenzene) to ethylene molar ratio of 1-10, more preferably of 1-5, and ideally of 1.5-2.5. Preferably, the ethylene can be injected at various points along the alkylation reaction zone. In such aspects, the ethylene is typically injected at 1, 2, 3, 4, or 5 separate sites along the reaction zone. In another embodiment, a Lewis acid catalyst can be used, such as $AlCl_3$. The preferred alkylation catalyst comprises a molecular sieve of the MWW framework type (as described in the hydroalkylation section—but without metal). In any embodiment, the amount of catalyst is preferably selected such that the ethylene consumption is greater than about 80%, preferably greater than about 90%, and ideally about 100%. Generally, the corresponding monomer (e.g., cyclohexylbenzene) conversion varies depending on the monomer to ethylene molar ratio. Preferably, the monomer (e.g., cyclohexylbenzene) consumption is greater than about 1%, or greater than about 30%, or greater than about 50%, or about 100%. Examples of suitable alkylation processes can be found in U.S. Pat. Nos. 5,600,048; 3,751,504; 7,399,894; and 7,939,700, the entire contents of which are incorporated herein by reference.

Typically, the ethyl alkylation reaction product comprises a mixture of CHEB isomers having a ratio of 2- to 3- to 4-isomers of about 1:2:1. Preferably, the ethyl alkylation product comprises a mixture of CHEB isomers comprising greater than about 5 wt %, or greater than about 10 wt %, or greater than about 20 wt % of the 2-isomer, greater than about 5 wt %, or greater than about 10 wt %, or greater than about 20 wt % of the 4-isomer, and greater than about 10 wt %, or greater than about 30 wt %, or greater than about 50 wt % of the 3-isomer. Additionally or alternatively, the ethyl alkylation product may comprise a mixture of CHEB isomers comprising less than about 20 wt %, or less than about 10 wt %, of the 2-isomer, less than about 20 wt %, or less than about 10 wt %, of the 4-isomer, and less than about 30 wt %, or less than about 20 wt %, of the 3-isomer.

The final reaction stage then comprises dehydrogenation of the desired cyclohexylethylbenzene isomer(s), for example, 1-cyclohexyl-4-ethylbenzene, to the corresponding isomer(s) of phenylstyrene, for example, 4-vinylbiphenyl.

In one embodiment, the dehydrogenation may be conducted in a single step in the presence of a dehydrogenation catalyst comprising a metal or oxide form of Fe, K, Cr, Mo, Ce, Zn, Bi, Ca, Co, Cu, Li, Mg, V, W, Zr, Ti, Mn, B, Al, Si, Pt, Pd, Ni, Ru, Re, Sn, Na, or any combination thereof. Preferably, the dehydrogenation is conducted in the presence of an inhibitor to prevent polymerization of the dehydrogenation product. The inhibitor is preferably present in an amount of from about 1 ppm to about 100 ppm. The dehydrogenation may be conducted in the presence of a hydrogen and/or steam co-feed, for example, such that the molar ratio of $H_2/H_2O$:hydrocarbon is from 0.5 to 12, such as from 0.5 to 10, or from 1 to 4.

A suitable catalyst to effect the desired dehydrogenation comprises an inorganic support comprising 0.05 wt % to 2 wt % of a metal selected from Group 14 of the Periodic Table of Elements; such as tin, and 0.1 wt % to 5 wt % of a metal selected from Groups 6 to 10 of the Periodic Table of Elements, such as nickel, platinum and/or palladium, the weight percents being based upon total weight of the first catalyst. Conveniently, the support is selected from the group consisting of alumina, silica, a silicate, an aluminosilicate, zirconia, titania and carbon nanotubes, and preferably comprises silica. Suitable dehydrogenation conditions include a temperature of about 250° C. to about 700° C., such as about 250° C. to about 600° C., or from about 390° C. to about 480° C., or from about 350° C. to about 450° C., a pressure of about 10 kPa-a to about 21000 kPa-a, such as from about 100 kPa to about 7000 kPa, a weight hourly space velocity of about 0.2 $hr^{-1}$ to about 50 $hr^{-1}$, such as from about 1 $hr^{-1}$ to about 10 $hr^{-1}$, and a hydrogen to hydrocarbon feed molar ratio of about 0 to about 20. Preferably, interstage heating may be employed in the dehydrogenation reaction stage. The dehydrogenation may be conducted in the presence of a hydrogen and/or steam co-feed, for example, such that the molar ratio of $H_2/H_2O$:hydrocarbon is from 0.5 to 12, such as from 0.5 to 10, or from 1 to 4.

In another embodiment, the dehydrogenation proceeds in two steps, namely (i) dehydrogenation of the cyclohexylethylbenzene with a first dehydrogenation catalyst to produce a first dehydrogenation product comprising ethylbiphenyl and then (ii) dehydrogenation of at least part of the ethylbiphenyl in the first dehydrogenation product with a second dehydrogenation catalyst to produce a second dehydrogenation product comprising phenylstyrene. A suitable first dehydrogenation catalyst comprises an inorganic support comprising 0.05 wt % to 2 wt % of a metal selected from Group 14 of the Periodic Table of Elements; such as tin, and 0.1 wt % to 5 wt % of a metal selected from Groups 6 to 10 of the Periodic Table of Elements, such as nickel, platinum, and/or palladium, the weight percents being based upon total weight of the first catalyst. Generally, the Group 14 metal is present in the dehydrogenation catalyst in an amount of at least 0.05 wt %, at least 0.1 wt %, at least 0.15 wt %, at least 0.2 wt %, at least 0.3 wt %, at least 0.4 wt %, or at least 0.5 wt %, or at least 1 wt %, or at least 5 wt % based upon total weight of the dehydrogenation catalyst. In one embodiment, the Group 14 metal is tin. In various embodiments, the Group 14 is present in an amount between 0.05 wt % and 5 wt %, or 0.05 wt % and 1 wt %, or 0.05 wt % and 0.5 wt % of the catalyst or between 0.1 wt % and 0.4 wt % of the catalyst or between 0.1 wt % and 0.3 wt %, or between about 0.15 wt % and 0.2 wt % of the dehydrogenation catalyst. Conveniently, the support is selected from the group consisting of silica, a silicate, an aluminosilicate, zirconia, titania, and carbon nanotubes, and preferably comprises silica. Suitable dehydrogenation conditions include a temperature of about 250° C. to about 700° C., such as about 250° C. to about 600° C., or from about 390° C. to about 480° C., or from about 350° C. to about 450° C., a pressure of about 10 kPa-a to about 21000 kPa-a, such as from about 100 kPa to about 7000 kPa, a weight hourly space velocity of about 0.2 hr$^{-1}$ to about 50 hr$^{-1}$, such as from about 1 hr$^{-1}$ to about 10 hr$^{-1}$, and a hydrogen to hydrocarbon feed molar ratio of about 0 to about 20, such as from 0.5 to 12, or from 0.5 to 10, or from 1 to 4. Suitable materials for the second dehydrogenation catalyst comprises an oxide or metal form of Fe, K, Cr, Mo, Ce, Zn, Bi, Ca, Co, Cu, Li, Mg, V, W, Zr, Ti, Mn, B, Al, Si, Pt, Pd, Ni, Ru, Re, Sn, Na, or any combination thereof. Suitable conditions for the second dehydrogenation step comprise a temperature from 400 to 700° C. and a pressure from 100 to 3550 kPa-a. Either or both of the first and second dehydrogenation steps can be conducted in the presence of a hydrogen and/or steam co-feed, for example, such that the molar ratio of $H_2/H_2O$:hydrocarbon is from 0 to 12, such as from 0 to 12, such as from 0 to 10, or from 1 to 4.

Irrespective of whether the cyclohexylethylbenzene dehydrogenation is conducted in one or two steps, the dehydrogenation effluent will contain co-produced hydrogen and residual cyclohexylethylbenzene in addition to the desired phenylstyrene product. The co-produced hydrogen can readily be flashed from the effluent and recycled to, for example, the dehydrogenation stage or the hydroalkylation stage. The residual cyclohexylethylbenzene can then be separated from the phenylstyrene in the effluent by, for example, distillation, for recycle back to the dehydrogenation stage, while the phenylstyrene is recovered for purification.

Irrespective of whether the cyclohexylethylbenzene dehydrogenation is conducted in one or two steps, preferably minimal to no isomerization occurs during dehydrogenation. For example, dehydrogenation of a mixture of CHEB isomers comprising less than about 2 wt %, or less than about 1 wt %, of the 2-isomer, greater than about 20 wt %, or greater than about 30 wt %, of the 4-isomer, and greater than about 40 wt %, or greater than 50 wt %, of the 3-isomer typically produces a mixture of ethylbiphenyl isomers comprising less than about 2 wt %, or less than about 1 wt %, of the 2-isomer, greater than about 20 wt %, or greater than about 30 wt %, of the 4-isomer, and greater than about 40 wt %, or greater than 50 wt %, of the 3-isomer and/or a mixture of vinylbiphenyl isomers comprising less than about 2 wt %, or less than about 1 wt %, of the 2-isomer, greater than about 20 wt %, or greater than about 30 wt %, of the 4-isomer. Similarly, dehydrogenation of a mixture of CHEB isomers comprising greater than about 5 wt %, or greater than about 10 wt %, or greater than about 20 wt % of the 2-isomer, greater than about 5 wt %, or greater than about 10 wt %, or greater than about 20 wt % of the 4-isomer, and greater than about 10 wt %, or greater than about 30 wt %, or greater than about 50 wt % of the 3-isomer typically produces a mixture of ethylbiphenyl isomers comprising greater than about 5 wt %, or greater than about 10 wt %, or greater than about 20 wt % of the 2-isomer, greater than about 5 wt %, or greater than about 10 wt %, or greater than about 20 wt % of the 4-isomer, and greater than about 10 wt %, or greater than 30 wt %, or greater than about 50 wt % of the 3-isomer and/or a mixture of vinylbiphenyl isomers comprising greater than about 5 wt %, or greater than about 10 wt %, or greater than about 20 wt % of the 2-isomer, greater than about 5 wt %, or greater than about 10 wt %, or greater than about 20 wt % of the 4-isomer, and greater than about 10 wt %, or greater than 30 wt %, or greater than about 50 wt % of the 3-isomer.

Conversion of Cyclohexylbenzene to Phenylstyrene Via Biphenyl or Conversion of Biphenyl to Phenylstyrene In other embodiments, the present reaction sequence for producing phenylstyrene proceeds via dehydrogenation of the cyclohexylbenzene generated in the benzene hydroalkylation stage to biphenyl, followed by ethylation of the biphenyl to ethylbiphenyl (EBP) and then dehydrogenation of the ethylbiphenyl to phenylstyrene. Alternatively, a biphenyl feedstock may be provided. In such aspects, the reaction sequence proceeds via ethylation of the biphenyl to ethylbiphenyl (EBP) and then dehydrogenation of the ethylbiphenyl to phenylstyrene.

In these embodiments, suitable catalysts and conditions for dehydrogenation of the cyclohexylbenzene to biphenyl are the same as those described above for dehydrogenation of cyclohexylethylbenzene isomer(s) to the corresponding isomer(s) of phenylstyrene.

Suitable catalysts and conditions for ethylation of the biphenyl to ethylbiphenyl are the same as those described above for the ethylation of cyclohexylbenzene to ethylcyclohexylbenzene. Generally, high temperatures (e.g., about 250° C. about 350° C.) and a high monomer (biphenyl) to ethylene molar ratio (e.g., 1-10) are useful for maximizing the production of ethylbiphenyl from biphenyl.

Preferably, the ethylation of biphenyl is particularly useful in the formation of the 2-isomer of EBP and, correspondingly, 2-vinylbiphenyl. Preferably, the ethyl alkylation product comprises a mixture of EBP isomers comprising greater than about 20 wt %, or greater than about 40 wt %, or greater than about 50 wt %, or greater than about 60 wt % of the 2-isomer, less than about 30 wt %, or less than about 15 wt %, of the 4-isomer, and less than about 50 wt %, or less than about 25 wt %, of the 3-isomer. Additionally or alternatively, the ethylation product may comprise a mixture of EBP isomers comprising less than about 80 wt %, or less than about 70 wt %, of the 2-isomer, greater than about 5 wt %, or greater than about 10 wt %, of the 4-isomer, and greater than about 10 wt %, or greater than about 20 wt %, of the 3-isomer.

Suitable catalysts and conditions for dehydrogenation of the ethylbiphenyl to phenylstyrene are also described above. Preferably, the dehydrogenation of ethylbiphenyl is conducted at high temperature (e.g., about 500° C. to about 600° C.) and using an $H_2O$ diluent. Particularly useful catalysts for the dehydrogenation of ethylbiphenyl to phenylstyrene include Fe based mixed metal oxides, preferably further comprising Cr, Mg, or Na. Often, interstage heating may be employed in the dehydrogenation reaction stage in the dehydrogenation of ethylbiphenyl. Alternatively, the dehydrogenation may be conducted without employing interstage heating. The dehydrogenation effluent will generally contain residual ethylbiphenyl in addition to the desired phenylstyrene product. The residual ethylbiphenyl can then be separated from the phenylstyrene in the effluent by, for example, distillation, for recycle back to the dehydrogenation stage, while the phenylstyrene is recovered for purification.

Preferably minimal to no isomerization occurs during dehydrogenation. For example, dehydrogenation of a mixture of ethylbiphenyl isomers comprising greater than about 20 wt %, or greater than about 40 wt %, or greater than about 50 wt %, or greater than about 60 wt % of the 2-isomer, less than about 30 wt %, or less than about 15 wt %, of the 4-isomer, and less than about 50 wt %, or less than about 25 wt %, of the 3-isomer typically produces a mixture of vinylbiphenyl isomers comprising greater than about 20 wt %, or greater than about 40 wt %, or greater than about 50 wt %, or greater than about 60 wt % of the 2-isomer, less than about 30 wt %, or less than about 15 wt %, of the 4-isomer, and less than about 50 wt %, or less than about 25 wt %, of the 3-isomer.

Referring now to the drawing, a simplified process flow diagram of one embodiment of the present reaction sequence via ethylcyclhexylbenzene is shown in FIG. 1, in which benzene and hydrogen are supplied via line 11 to a hydroalkylation reactor 12, which is operated under conditions effective to hydroalkylate the benzene to produce cyclohexylbenzene. Effluent from the hydroalkylation reactor 12 comprises unreacted benzene and, in some cases unreacted hydrogen, in addition to the cyclohexylbenzene and is fed via line 13 to a first separation system 14, where the benzene and hydrogen are removed and recycled via line 15 back to the hydroalkylation reactor 12.

Cyclohexylbenzene is recovered from the hydroalkylation effluent by the first separation system 14 and is fed via line 16 to a transalkylation reactor 17, which also receives an ethylbenzene feed from line 18. The transalkylation reactor 17 is operated under conditions effective for the ethylbenzene to react with the cyclohexylbenzene to produce a transalkylation effluent comprising a mixture of cyclohexylethylbenzene isomers and benzene in addition to residual ethylbenzene and cyclohexylbenzene. The effluent from the transalkylation reactor 17 is collected in line 19 and fed to a second separation system 21.

The second separation system 21 comprises a plurality of distillation columns, which are operated to separate the transalkylation effluent into at least the following fractions:
(a) a benzene-containing fraction, which is removed via line 22 for recycle to the hydroalkylation reactor 12;
(b) an ethylbenzene-containing fraction, which is removed via line 23 for recycle to the transalkylation reactor 17;
(c) a cyclohexylbenzene-containing fraction, which is removed via line 24 for recycle to the transalkylation reactor 17; and
(d) a cyclohexylethylbenzene-containing fraction, which is removed via line 25 for supply to a dehydrogenation reactor 26.

In some embodiments, the second separation system 21 includes provision for separating the cyclohexylethylbenzene isomers into one or more desired isomers, for example, 1-cyclohexyl-4-ethylbenzene, which are removed in line 25 and one or more undesired isomers, for example, 1-cyclohexyl-2-ethylbenzene and 1-cyclohexyl-3-ethylbenzene, which can be recycled, for example, via line 24, to the transalkylation reactor 17.

The dehydrogenation reactor 26 is operated under conditions to dehydrogenate the cyclohexylethylbenzene isomer(s) supplied via line 25 to produce a dehydrogenation effluent containing one or more phenylstyrene isomers together with co-produced hydrogen and residual cyclohexylethylbenzene. The dehydrogenation effluent is supplied via line 27 to a third separation system 28, where the hydrogen is removed via line 29 for recycle to the hydroalkylation reactor 12 or the dehydrogenation reactor 26 and the residual cyclohexylethylbenzene is removed via line 31 for recycle to the dehydrogenation reactor 26. The phenylstyrene is recovered by line 32 and sent to product purification.

The invention will now be more particularly described with reference to the following non-limiting Examples.

Samples were analyzed on an Agilent 7890 GC equipped with a 5975C MSD detector and FID. Typical injection size was about 0.5 µl. The columns used were from Supelco of the Dex type. A Gamma DEX column was joined together with a Beta Dex column to give a total length of 120 m (60 m for each type). The internal diameter of the columns was 0.25 mm. This setup had a purged 2-way splitter that enabled a sample to be simultaneously analyzed on two detectors using a single injection. Additionally, an auxiliary helium pressure of 6 psi was used for the purged splitter. The system was operated in constant flow mode with an initial pressure of about 78 psi and column flow of about 3.0 m/min using helium as carrier gas. The following oven procedure was utilized:

Initial temperature of 140° C. and pressure of 78 psi, hold for 30 minutes,
Ramp 1 at 2° C./min to 180° C., hold for 20 minutes,
Ramp 2 at 3° C./min to 220° C., hold for 27 minutes, and
Total analysis time of about 1 to 10 minutes.

EXAMPLE 1

Transalkylation of Cyclohexylbenzene

The experiments reported in Example 1 were conducted in a reactor consisting of a quartz tube of 9 mm in diameter heated by a furnace. Annular $N_2$ flow on the outside of the quartz reactor allowed for pressure equilibration between the inside and outside of the reactor channel USY catalyst extrudates were crushed to 20/40 mesh and 2 g of the crushed extrudates were loaded into the reactor after being diluted up to 4 g in crushed quartz. A quartz wool plug was used at the top and bottom of the catalyst bed to keep catalyst in place. The reactor contained an internal thermocouple in the catalyst bed in a ⅛" thermowell. The reactor was topped off with the same quartz chips.

The catalyst was dried overnight under $N_2$ at 290° C. An ISCO syringe pump was used to introduce the feed to the reactor. The feed was pumped through a vaporizer before being mixed in-line with $N_2$ at a molar ratio of 0.7 (gas to hydrocarbon liquid). The products exiting the reactor were condensed, collected, and analyzed off-line by GCMS in accordance with the above described procedure.

To study the transalkylation of cyclohexylbenzene with ethylbenzene, a liquid feed consisting of 67% ethylbenzene and 33% cyclohexylbenzene was fed over the USY catalyst in the reactor described above at a pressure of 165 psig (1239 kPa-a) and a temperature of 165° C. The total WHSV was 1 $hr^{-1}$. Under these conditions, a cyclohexylbenzene conversion of 39% was achieved. Table 1 shows the weight percent of each species in the reactor liquid effluent as determined by the analysis procedure described.

TABLE 1

| Species | Effluent Liquid Wt % |
|---|---|
| Non-aromatic lights | 0.4 |
| Benzene | 6.1 |
| Toluene | 1.2 |
| Xylenes | 0.5 |
| Ethylbenzene | 54.6 |
| Diethylbenzene | 2.1 |
| Cyclohexylbenzene | 20.0 |
| Cyclohexylethylbenzenes | 12.1 |
| Other heavies | 3.1 |

As can be seen from Table 1, reasonable yields of cyclohexylethylbenzene (multiple isomers) can be achieved under moderate operating conditions via the transalkylation reaction of cyclohexylbenzene and ethylbenzene. Byproducts include light aromatics from cracking or disproportionation, diethylbenzene from ethyl disproportionation and other heavies resulting from multiple alkylation reactions. Overall, the selectivity toward cyclohexylethylbenzene is 80% (moles cyclohexylethylbenzene produced per mole cyclohexylbenzene consumed).

To study the isomer distribution formed from the transalkylation of cyclohexylbenzene with ethylbenzene, the transalkylation reaction was repeated using the same conditions described above with the exception of operating at a slightly higher temperature of 170° C. The weight percent of the CHEB isomers in the reactor liquid effluent were then determined by the analysis procedure described. Under these conditions, no measurable amount of 2-CHEB was observed. Additionally, 3-CHEB was present in the effluent at 8.4 wt % and 4-CHEB was present in the effluent at 4.2 wt %, That is, the observed isomer distribution was a ratio of 3-:4-CHEB isomers of 2:1 with negligible to no 2-isomer.

EXAMPLE 2

Synthesis of Alkylation Catalyst 80 parts MCM-49 crystal were combined with 20 parts pseudoboehmite alumina, on a calcined dry weight basis. The MCM-49 and pseudoboehmite alumina dry powder were placed in a muller or a mixer and mixed for about 10 to 30 minutes. Sufficient water was added to the MCM-49 and alumina during the mixing process to produce an extrudable paste. The extrudable paste was formed into a 1/20 inch quadralobe extrudate using an extruder. After extrusion, the 1/20th inch quadralobe extrudate was dried at a temperature ranging from 250° F. (121° C.) to 325° F. (163° C.). After drying, the dried extrudate was heated to 1000° F. (538° C.) under flowing nitrogen, then ion exchanged with 0.5 to 1 N ammonium nitrate solution after cooling. The ammonium nitrate exchanged extrudate was then dried and then calcined in a nitrogen/air mixture to a temperature of 1000° F. (538° C.).

EXAMPLE 3

Alkylation of Cyclohexylbenzene

Figure 2:
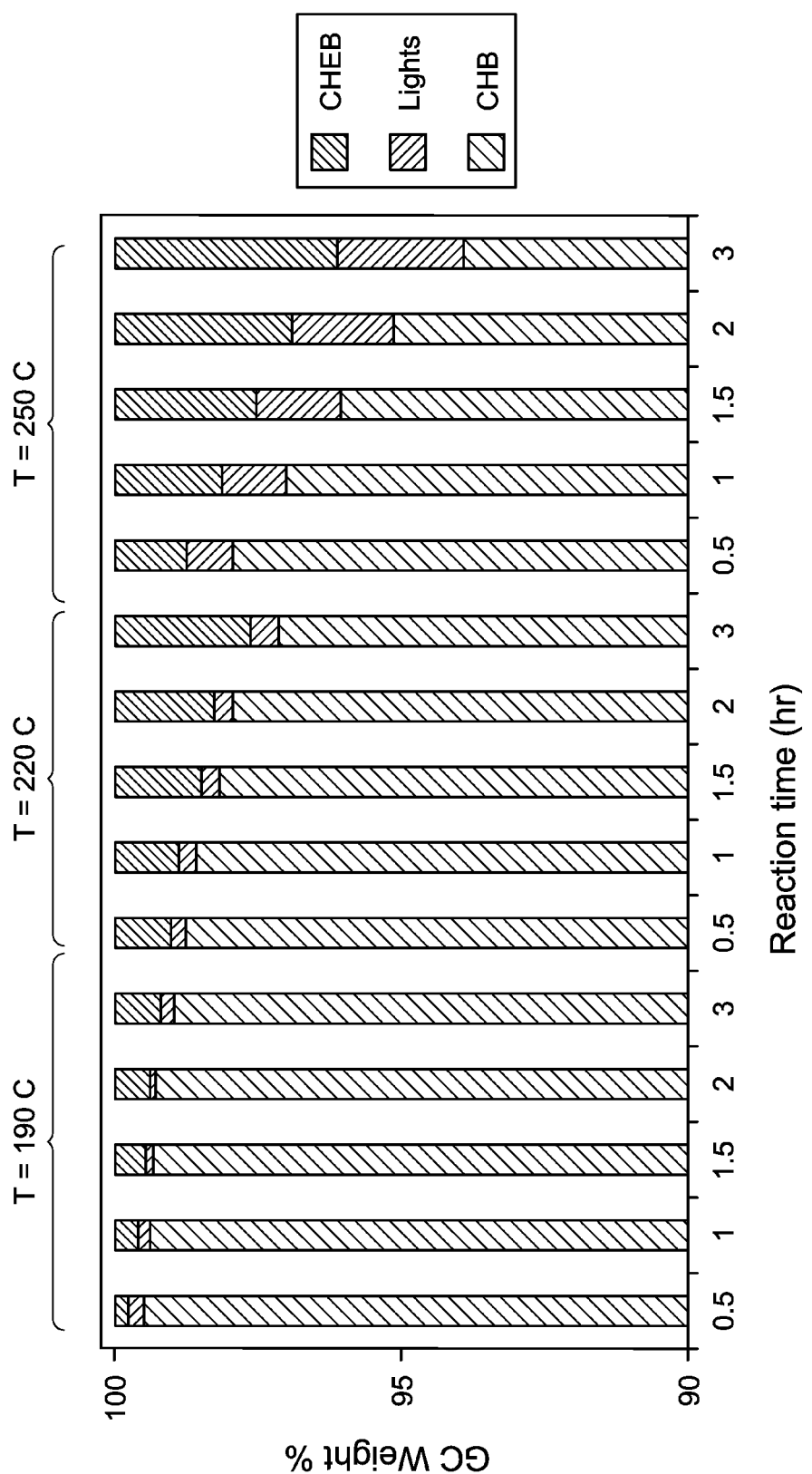
FIG. 2 is a graph for Example 3 showing the composition of the reactor effluent against time-on-stream (TOS) at various reactor temperatures in the alkylation of cyclohexylbenzene (CHB). Conditions: 450-550 psig (3100-3800 kPa-g); 190-250° C.; 1 gmol CHB (initial); and CHB: Ethylene=3.5:1 (molar basis).

To study the alkylation of cyclohexylbenzene with ethylene, 0.25 g of the alkylation catalyst of Example 2 along with a feed consisting of 1 gmol of cyclohexylbenzene (CHB) and 0.29 gmol of ethylene (3.5:1 molar ratio of CHB to ethylene) were charged into a 300 ml Parr reactor at a pressure of 165 psig (1239 kPa-a). The reactor was then heated to a temperature ranging from 190° C. to 250° C. FIG. 2 shows the weight percent of each species in the reactor liquid effluent against time-on-stream (TOS) in the reactor at three operating temperatures (190° C., 220° C., and 250° C.) as determined by the above described analysis procedure. Table 2 shows the ratio of CHEB isomers to light byproducts (by weight percent) in the reactor liquid effluent after 1.5 h TOS.

TABLE 2

| Temperature (° C.) | Ratio |
|---|---|
| 190 | 4.99 |
| 220 | 4.98 |
| 250 | 1.67 |

As can be seen from FIG. 2 and Table 2, reasonable selectivity towards cyclohexylethylbenzene (CHEB) (multiple isomers) can be achieved under moderate operating conditions via the alkylation reaction of cyclohexylbenzene and ethylene. The conversion of CHB could likely be increased by conducting the reaction in a flow reactor as opposed to a batch reactor. Primary byproducts include light aromatics from cracking or disproportionation. The typical isomer distribution observed over the range of tested temperatures was a ratio of 2-:3-:4-CHEB isomers of 1:2:1. For example, at an operating temperature of 250° C. and 3 h TOS, the observed isomer distribution in the effluent was 0.88 wt % 2-CHEB, 2.05 wt % 3-CHEB, and 0.97 wt % 4-CHEB. That is, the alkylation reaction pathway of CHB resulted in a different isomer distribution than the transalkylation reaction pathway (e.g., higher selectivity towards 2-CHEB isomers).

EXAMPLE 4

Alkylation of Biphenyl

Figure 3:
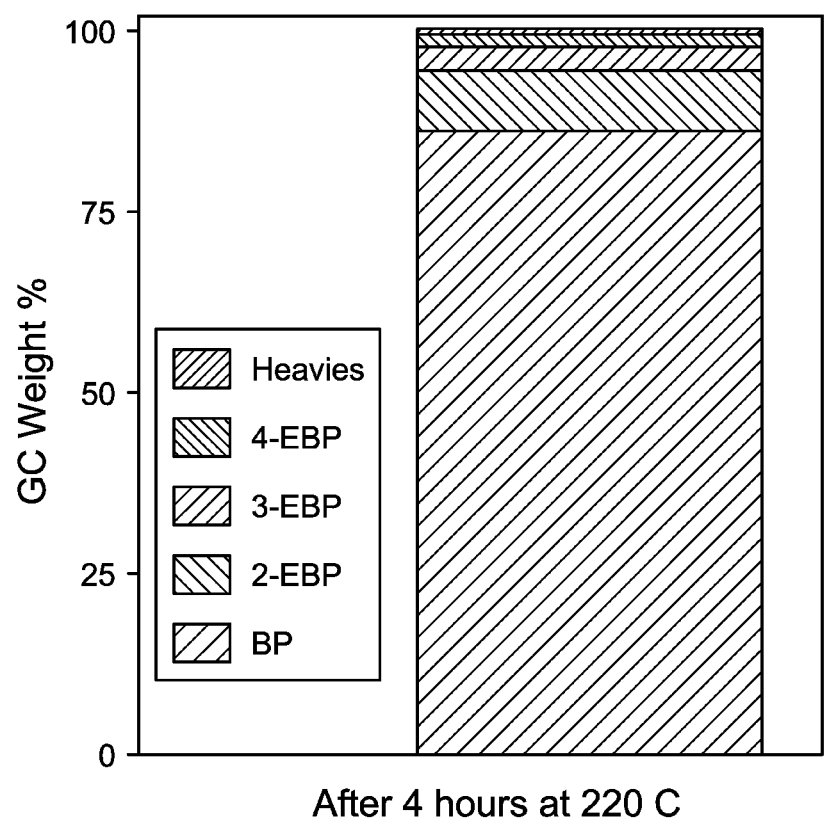
FIG. 3 is a graph for Example 4 showing the composition of the reactor effluent in the alkylation of biphenyl (BP). Conditions: 450-550 psig (3100-3800 kPa-g); 220° C.; 1 gmol BP (initial); BP:Ethylene=3.5:1 (molar basis); and 4 h TOS.

To study the alkylation of biphenyl with ethylene, 0.25 g of the alkylation catalyst of Example 2 along with a feed consisting of 1 gmol of biphenyl (BP) and 0.29 gmol of ethylene (3.5:1 molar ratio of BP to ethylene) were charged into a 300 ml Parr reactor at a pressure ranging from 450-550 psig (3100-3800 kPa-g). The reactor was then heated to a temperature of 220° C. The obtained reactor product was dissolved in toluene for analysis. FIG. 3 shows the weight percent of each species in the reactor product after 4 h TOS determined by the above described analysis procedure (after correcting for the presence of toluene).

As can be seen from FIG. 3, reasonable selectivity towards ethylbiphenyl (E B P) (multiple isomers) can be achieved under moderate operating conditions via the alkylation reaction of biphenyl and ethylene. The conversion of BP could likely be increased by conducting the reaction in a flow reactor as opposed to a batch reactor. Primary byproducts include heavies resulting from multiple alkylation reactions. As can also be seen from FIG. 3, the typical isomer distribution observed was a ratio of 2-:3-:4-EBP isomers of 63:23:14. More specifically, the observed isomer distribution in the product was 8.18 wt % 2-EBP, 3 wt % 3-EBP, and 1.86 wt % 4-EBP. That is, the alkylation reaction pathway of BP resulted in high selectivity towards 2-EBP isomers.

EXAMPLE 5

Dehydrogenation of Cyclohexylethylbenzene

The experiments reported in Examples 5 A and B were conducted in flow reactors consisting of stainless steel tubes ¾ in (19 mm) in diameter. Catalyst extrudates were crushed to 20/40 mesh and loaded into the reactor in quantities ranging from 0.25-1 g (to vary corresponding weight based space velocity). A quartz wool plug was used at the top and bottom of the catalyst bed to keep catalyst in place. The reactors were placed in heated furnaces to control isothermal reaction temperature. Each reactor contained an internal thermocouple in the catalyst bed. The reactors were topped off with the same quartz chips.

The catalyst was pre-conditioned in situ by heating under hydrogen under a slow ramp to maximum temperatures of ~500° C. An ISCO syringe pump was used to introduce the feed to the reactor. The feed was pumped through a vaporizer before being mixed in line with $H_2$. The feed was then pumped through the catalyst bed held at the reaction temperature. An Inhibitor (NACLO EC 3355 A) was added (5 ppm) to the reactor to prevent polymerization of product. The products exiting the reactor were condensed and collected in intervals (approximately one sample per day per reactor) and analyzed off-line by GCMS in accordance with the above described procedure.

EXAMPLE 5A

Dehydrogenation of 1-Cyclohexyl-2-Ethylbenzene (2-CHEB)

Figure 4:
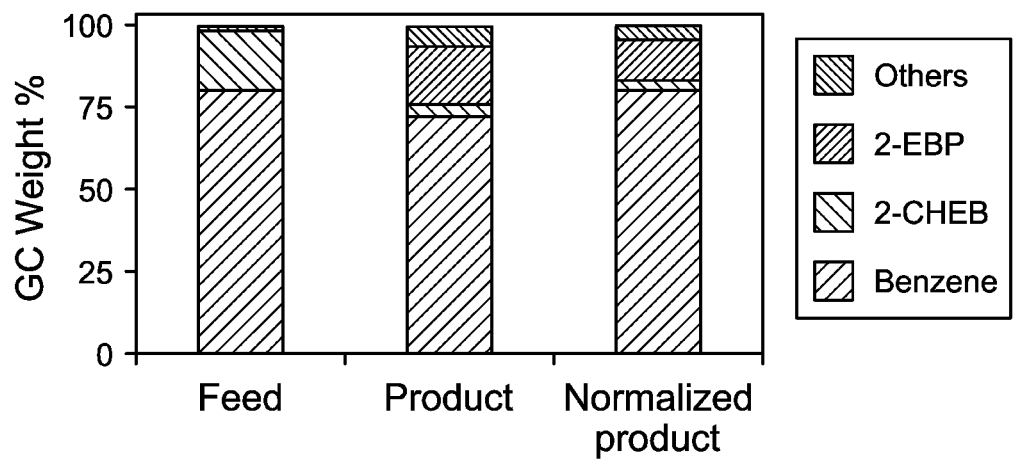
FIG. 4 is a graph for Example 6A showing the compositions of the hydrocarbon (HC) feed and reactor effluent in the dehydrogenation of 1-cyclohexyl-2-ethylbenzene (2-CHEB). Conditions: WHSV=10 h$^{-1}$; 100 psig (690 kPa-g); 425° C.; and Hydrogen:HC Feed=2:1 (molar basis).

To study the dehydrogenation of 2-CHEB, a feed consisting of 20% 2-CHEB and balance benzene was fed over a Pt/Sn dehydrogenation catalyst on silica support in the reactor described above at a pressure of 100 psig (690 kPa-g, a temperature of 425° C., a hydrogen to hydrocarbon molar ratio of 2, and a total WHSV of 10 $h^{-1}$. FIG. 4 and Table 3 show the weight percent of each species in the feed and reactor effluent. The product data of FIG. 4 and Table 3 represents the raw data obtained from the GC, and the normalized product data represents estimates the actual percentage of each species in the effluent after accounting for benzene loss to atmosphere during measurement.

TABLE 3

| Species | Feed Wt % | Product Wt % | Normalized Product Wt % |
|---|---|---|---|
| Benzene | 80.0 | 72.7 | 80.0 |
| 2-CHEB | 18.6 | 3.99 | 2.93 |
| 2-EBP | 0.00 | 18.8 | 13.8 |
| Other | 1.40 | 4.48 | 3.29 |

As can be seen from FIG. 4 and Table 3, high conversion (>80%) of 2-CHEB and high selectivity (>80%) towards the desired dehydrogenated product, ethylbiphenyl, was obtained. As can also be seen from FIG. 4 and Table 3, all obtained ethylbiphenyl exhibited the ethyl group in the 2 position (i.e., no isomerization activity was observed).

EXAMPLE 5B

Dehydrogenation of 1-Cyclohexyl-4-Ethylbenzene (4-CHEB)

Figure 5:
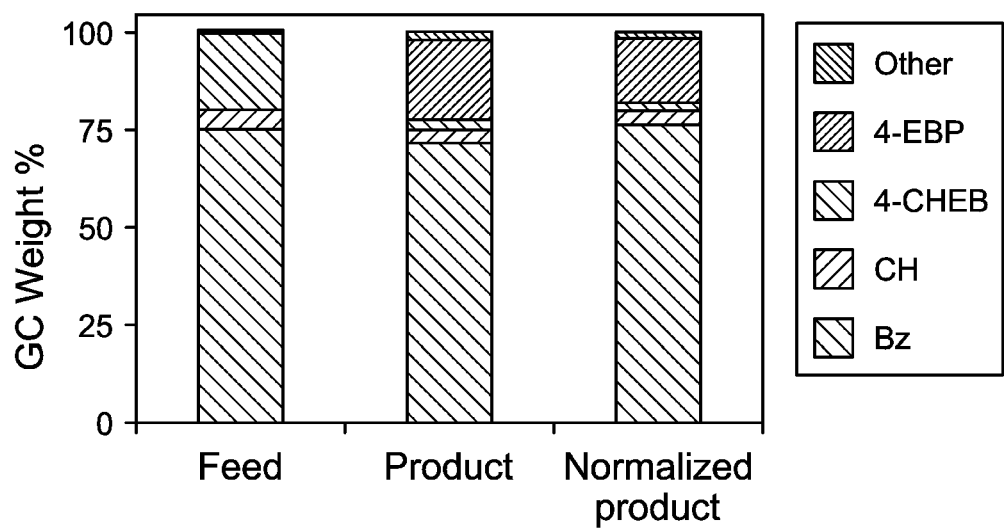
FIG. 5 is a graph for Example 6B showing the compositions of the HC feed and reactor effluent in the dehydrogenation of 4-ethylcyclohexylbenzene (4-CHEB). Conditions: 100 psig (690 kPa-g); 450° C.; and Hydrogen:HC Feed=2:1 (molar basis).

To study the dehydrogenation of 4-CHEB, a feed consisting of 20% 4-CHEB, 5% cyclohexane (CH), and balance benzene (bz) was fed over a Pt/Sn dehydrogenation catalyst on silica support in the reactor described above at a pressure of 100 psig (690 kPa-g, a temperature of 450° C., a hydrogen to hydrocarbon molar ratio of 2, and a total WHSV of 10 $h^{-1}$. FIG. 5 and Table 4 shows the weight percent of each species in the feed and reactor effluent. The product data of FIG. 5 and Table 4 represents the raw data obtained from the GC, and the normalized product data represents estimates the actual percentage of each species in the effluent after accounting for benzene loss to atmosphere during measurement.

TABLE 4

| Species | Feed Wt % | Product Wt % | Normalized Product Wt % |
|---|---|---|---|
| Benzene | 76.0 | 71.5 | 76.3 |
| Cyclohexane | 4.93 | 3.51 | 3.75 |
| 4-CHEB | 18.8 | 2.12 | 1.70 |
| 4-EBP | 0.250 | 21.0 | 16.8 |
| Other | 0.00 | 1.85 | 1.48 |

As can be seen from FIG. 5 and Table 4, high conversion (>85%) of 4-CHEB and high selectivity (ca. 80%) towards the desired dehydrogenated product, ethylbiphenyl, was obtained. As can also be seen from FIG. 5 and Table 4, all obtained ethylbiphenyl exhibited the ethyl group in the 4 position (i.e., no isomerization activity was observed).

All documents described herein are incorporated by reference herein, including any priority documents and/or testing procedures to the extent they are not inconsistent with this text. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including." Likewise, whenever a composition, an element or a group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa.

What is claimed is:

1. A process for producing phenylstyrene, the process comprising:
    (a1) contacting benzene with hydrogen in the presence of a hydroalkylation catalyst under conditions effective to produce a hydroalkylation product comprising cyclohexylbenzene;
    (b1) converting at least part of the cyclohexylbenzene from (a1) to cyclohexylethylbenzene by contacting the cyclohexylbenzene with ethylbenzene in the presence of a transalkylation catalyst under conditions effective to produce a transalkylation product comprising cyclohexylethylbenzene; and/or contacting the cyclohexylbenzene with ethylene in the presence of an alkylation catalyst under conditions effective to produce an alkylation product comprising cyclohexylethylbenzene; and
    (c1) contacting at least part of the cyclohexylethylbenzene from (b1) with at least one dehydrogenation catalyst under conditions effective to produce a dehydrogenation product comprising phenylstyrene.

2. The process of claim 1, wherein the contacting (a1) is conducted under conditions including a temperature from about 100° C. to about 400° C. and a pressure from about 100 to about 7,000 kPa.

3. The process of claim 1, wherein the hydroalkylation catalyst comprises an acidic component and a hydrogenation component.

4. The process of claim 3, wherein the acidic component of the hydroalkylation catalyst comprises a molecular sieve.

5. The process of claim 4, wherein the molecular sieve comprises a molecular sieve of the MCM-22 family.

6. The process of claim 3, wherein the hydrogenation component of the hydroalkylation catalyst is selected from the group consisting of palladium, ruthenium, nickel, zinc, tin, cobalt, and compounds and mixtures thereof.

7. The process of claim 1, wherein a molar ratio of hydrogen to benzene supplied to the contacting (a1) is from about 0.15:1 to about 15:1.

8. The process of claim 1, wherein the converting (b1) comprises contacting the cyclohexylbenzene with ethylbenzene in the presence of a transalkylation catalyst under conditions including a temperature from about 100° C. to about 400° C. and a pressure from about 100 to about 10,000 kPa-absolute.

9. The process of claim 8, wherein the transalkylation catalyst comprises a molecular sieve.

10. The process of claim 8, wherein the transalkylation catalyst comprises a molecular sieve selected from the group consisting of BEA, FAU, MOR, MFI, MWW framework molecular sieves and mixtures thereof.

11. The process of claim 1, wherein the converting (b1) comprises contacting the cyclohexylbenzene with ethylene in the presence of an alkylation catalyst under conditions including a temperature from about 100° C. to about 500° C. and a pressure from about 100 to about 10,000 kPa-absolute.

12. The process of claim 11, wherein the alkylation catalyst comprises a molecular sieve.

13. The process of claim 1, wherein the contacting (c1) to convert the cyclohexylethylbenzene to phenylstyrene is conducted in a single step.

14. The process of claim 13, wherein the contacting (c1) is conducted in the presence of a dehydrogenation catalyst comprising a metal or oxide form of Fe, K, Cr, Mo, Ce, Zn, Bi, Ca, Co, Cu, Li, Mg, V, W, Zr, Ti, Mn, B, Al, Si, Pt, Pd, Ni, Ru, Re, Sn, Na, or any combination thereof.

15. The process of claim 13, wherein the contacting (c1) is conducted in the presence of a hydrogen or steam co-feed.

16. The process of claim 1, wherein the contacting (c1) to convert the cyclohexylethylbenzene to phenylstyrene comprises:
 (i) contacting at least part of the cyclohexylethylbenzene from (b1) with a first dehydrogenation catalyst to produce a first dehydrogenation product comprising ethylbiphenyl; and
 (ii) contacting at least part of the ethylbiphenyl from (i) with a second dehydrogenation catalyst to produce a second dehydrogenation product comprising phenylstyrene.

17. The process of claim 16, wherein the first dehydrogenation catalyst comprises an element or compound thereof from Group 10 of the Periodic Table of the Elements and an element or compound thereof from Group 14 of the Periodic Table.

18. The process of claim 16, wherein the first dehydrogenation catalyst comprises silica.

19. The process of claim 17, wherein the second dehydrogenation catalyst comprises an oxide or metal form of Fe, K, Cr, Mo, Ce, Zn, Bi, Ca, Co, Cu, Li, Mg, V, W, Zr, Ti, Mn, B, Al, Si, Pt, Pd, Ni, Ru, Re, Sn, Na, or any combination thereof.

20. The process of claim 1, and further comprising:
 (d) separating at least part of the transalkylation product into a first fraction having an increased concentration of at least one isomer of cyclohexylethylbenzene as compared with the transalkylation product and a second fraction having a decreased concentration of at least one isomer of cyclohexylethylbenzene as compared with the transalkylation product;
 (e) supplying at least part of the first fraction to the contacting (c1); and
 (d) recycling the second fraction to the contacting (b1).

21. The process of claim 20, wherein the at least one isomer of cyclohexylethylbenzene comprises 1-cyclohexyl-4-ethylbenzene.

* * * * *